United States Patent
Cartellieri et al.

(10) Patent No.: US 9,574,437 B2
(45) Date of Patent: Feb. 21, 2017

(54) VISCOMETER FOR DOWNHOLE USE

(75) Inventors: Ansgar Cartellieri, Lower Saxony (DE); Stefan Sroka, Katy, TX (US)

(73) Assignee: BAKER HUGHES INCORPORATED, Houston, TX (US)

( * ) Notice: Subject to any disclaimer, the term of this patent is extended or adjusted under 35 U.S.C. 154(b) by 1057 days.

(21) Appl. No.: 13/556,677

(22) Filed: Jul. 24, 2012

(65) Prior Publication Data

US 2013/0025359 A1   Jan. 31, 2013

Related U.S. Application Data

(60) Provisional application No. 61/512,994, filed on Jul. 29, 2011.

(51) Int. Cl.
| | |
|---|---|
| E21B 47/00 | (2012.01) |
| E21B 47/06 | (2012.01) |
| E21B 49/08 | (2006.01) |
| G01N 11/08 | (2006.01) |

(52) U.S. Cl.
CPC ............ *E21B 47/06* (2013.01); *E21B 49/081* (2013.01); *G01N 11/08* (2013.01)

(58) Field of Classification Search
CPC .................................................... E21B 47/00
USPC ....................................... 73/152.02–152.11, 152.18–152.23,73/152.27–152.31, 152.43–152.46,73/152.51–152.55, 54.01, 54.02, 54.09
See application file for complete search history.

(56) References Cited

U.S. PATENT DOCUMENTS

| | | | |
|---|---|---|---|
| 4,299,118 A | 11/1981 | Gau et al. | |
| 4,742,094 A | 5/1988 | Brothers et al. | |
| 4,959,163 A | 9/1990 | Holtmyer et al. | |
| 4,982,793 A | 1/1991 | Holtmyer et al. | |
| 5,067,565 A | 11/1991 | Holtmyer et al. | |
| 5,149,370 A | 9/1992 | Olaussen et al. | |
| 5,546,791 A | 8/1996 | Meeten | |
| 5,674,817 A | 10/1997 | Brezinski et al. | |
| 5,723,416 A | 3/1998 | Liao | |
| 5,789,352 A | 8/1998 | Carpenter et al. | |
| 5,791,415 A | 8/1998 | Nguyen et al. | |
| 5,913,364 A | 6/1999 | Sweatman | |
| 5,968,255 A | 10/1999 | Mehta et al. | |
| 5,985,801 A | 11/1999 | Hoff | |

(Continued)

FOREIGN PATENT DOCUMENTS

| | | |
|---|---|---|
| CA | 1150974 | 8/1983 |
| CA | 2042993 | 11/1991 |

(Continued)

OTHER PUBLICATIONS

Gusler, et al. "A New Extreme-HP/HT Viscometer for New Drilling-Fluid Challenges" SPE 99009, IADC/SPE Drilling Conference, Miami, FL Feb. 21-23. Jun. 2007 SPE Drilling & Completion. pp. 81-89.

(Continued)

*Primary Examiner* — Michael A Lyons
*Assistant Examiner* — Hoang Nguyen
(74) *Attorney, Agent, or Firm* — Cantor Colburn LLP

(57) ABSTRACT

A method for measuring viscosity in a borehole includes: pumping downhole fluid through at least one tube disposed in a carrier configured to be disposed in a borehole in an earth formation; taking at least one differential pressure measurement of the fluid in the at least one tube via a pressure transducer; and estimating a viscosity of the fluid based on the differential pressure measurement.

20 Claims, 7 Drawing Sheets

(56) References Cited

U.S. PATENT DOCUMENTS

| | | | |
|---|---|---|---|
| 6,019,835 | A | 2/2000 | Chatterji et al. |
| 6,133,203 | A | 10/2000 | Estes et al. |
| 6,167,967 | B1 | 1/2001 | Sweatman |
| 6,176,323 | B1 * | 1/2001 | Weirich et al. ............. 175/40 |
| 6,192,986 | B1 | 2/2001 | Urlwin-Smith |
| 6,196,317 | B1 | 3/2001 | Hardy |
| 6,420,319 | B1 | 7/2002 | Estes et al. |
| 6,511,944 | B2 | 1/2003 | Taylor et al. |
| 6,831,108 | B2 * | 12/2004 | Dahanayake et al. ......... 516/69 |
| 6,898,963 | B2 * | 5/2005 | Irani ........................ 73/54.04 |
| 7,784,330 | B2 * | 8/2010 | Angelescu et al. ......... 73/54.09 |
| 2009/0049904 | A1 * | 2/2009 | Meister .................... 73/152.23 |
| 2009/0090504 | A1 * | 4/2009 | Weightman et al. .... 166/250.01 |
| 2011/0185805 | A1 * | 8/2011 | Roux et al. .............. 73/152.29 |

FOREIGN PATENT DOCUMENTS

| | | |
|---|---|---|
| CA | 2433589 | 1/2002 |
| CA | 2433586 | 7/2002 |
| CA | 2488090 A1 | 12/2003 |
| CA | 2488675 | 12/2003 |
| CA | 2441537 | 3/2004 |
| CA | 2506554 | 6/2004 |
| CA | 2510239 | 7/2004 |
| CA | 2461297 | 9/2004 |
| CA | 2526673 | 12/2004 |
| CA | 2483371 | 4/2005 |
| DE | 69519510 | 6/2001 |
| DE | 69903148 | 4/2003 |
| EP | 0458391 A1 | 5/1991 |
| EP | 0950795 A2 | 10/1999 |
| EP | 0953726 A1 | 11/1999 |
| GB | 2188162 | 9/1987 |

OTHER PUBLICATIONS

Notification of Transmittal of the International Search Report and the Written Opinion of the International Searching Authority, or the Declaration; PCT/US2012/048332; Jan. 29, 2013.

* cited by examiner

VISCOMETER FOR DOWNHOLE USE

CROSS REFERENCE TO RELATED APPLICATIONS

This application claims the benefit of an earlier filing date from U.S. Provisional Application Ser. No. 61/512,994 filed Jul. 29, 2011, the entire disclosure of which is incorporated herein by reference.

BACKGROUND

Viscometric analysis can be useful for evaluating fluids in a variety of applications, such as subterranean applications. For example, viscometric analysis can be useful for in-situ characterization of downhole fluids. Such characterization can deliver information about, for example, a clean up process during downhole fluid sampling. Viscosity data can also assist with estimation of the American Petroleum Institute ("API") grade of the reservoir oil as well as production planning.

SUMMARY

A method for measuring viscosity in a borehole includes: pumping downhole fluid through at least one tube disposed in a carrier configured to be disposed in a borehole in an earth formation; taking at least one differential pressure measurement of the fluid in the at least one tube via a pressure transducer; and estimating a viscosity of the fluid based on the differential pressure measurement.

An apparatus for measuring viscosity of a fluid in a borehole includes: a carrier configured to be disposed in a borehole in an earth formation, the carrier including at least one tube configured to contain at least one sample of the fluid; at least one pump configured to establish flow in the at least one tube; at least one pressure transducer configured to measure a differential pressure in each of the at least one tube; and a processor configured to estimate a viscosity of the fluid based on the differential pressure measurement.

BRIEF DESCRIPTION OF THE FIGURES

The invention will now be described by way of non-limiting example with respect to the following figures.

DETAILED DESCRIPTION

Figure 1:
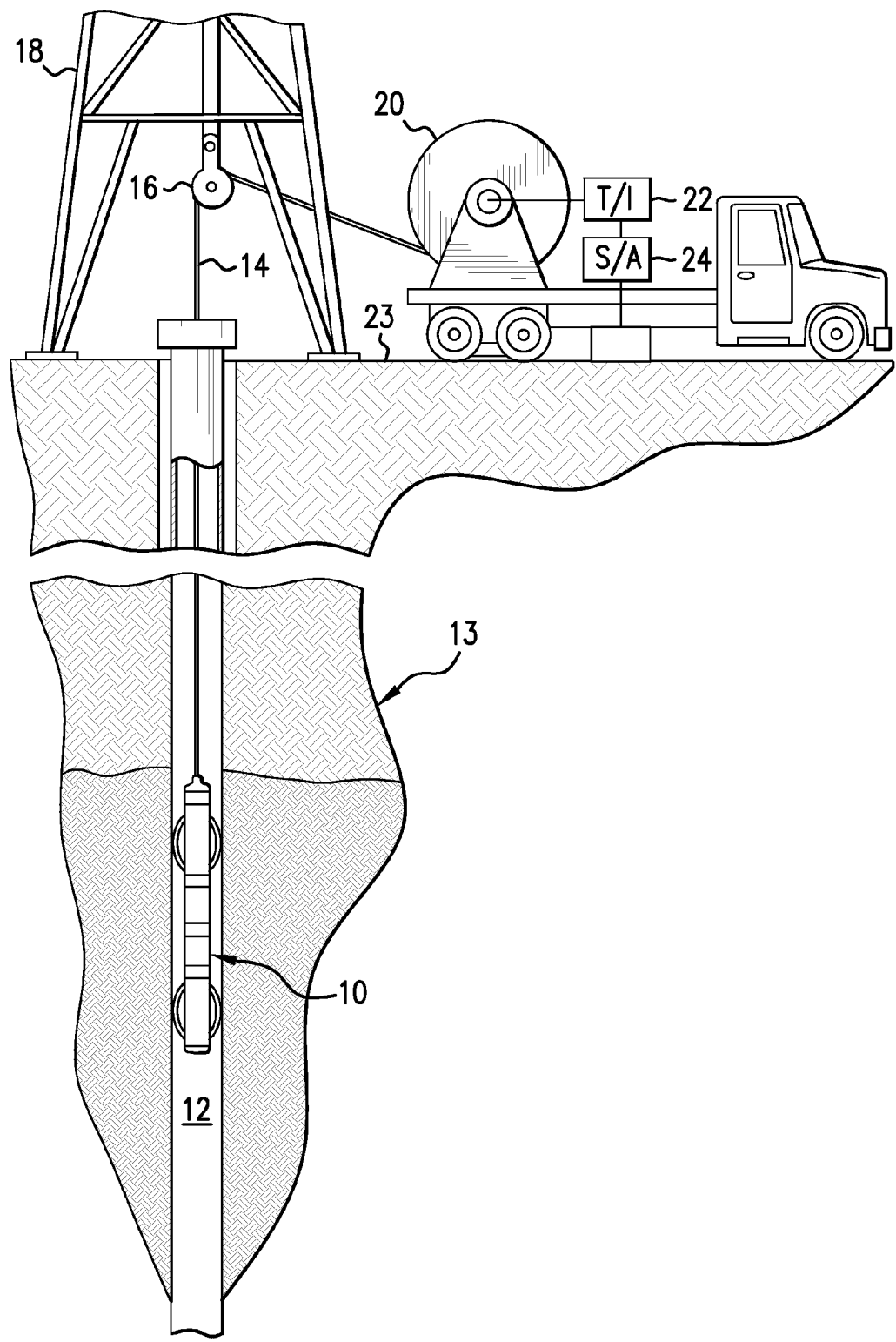
FIG. 1 is a vertical section of a downhole drilling, monitoring, evaluation, exploration and/or production system that includes a viscometer.

FIG. 1 describes a section of a downhole drilling, monitoring, evaluation, exploration and/or production system that includes a viscometer. A downhole tool 10 such as a wireline tool or sonde is suspended in a borehole 12 that penetrates earth formation 13. The downhole tool 10 may be suspended from cable 14 that passes over a sheave 16 mounted on a drilling rig 18. Cable 14 provides support for, power to, and/or data to and from the receptacle 10. Draw works 20 are configured to raise and lower the downhole tool 10. Electronic module 22, on the surface 23, may be included for transmitting operating commands downhole and/or receiving data from the downhole tool 10. The data may be recorded on an archival storage medium of any desired type for concurrent or later processing. Data processing apparatus 24, such as a suitable computer, may perform data analysis in the field in real time. Alternatively, or in addition, recorded data may be sent to a processing center for post processing or be stored and/or processed downhole.

The downhole tool 10 is not limited to the embodiments described herein, and may be disposed with any suitable carrier. A "carrier" as described herein means any device, device component, combination of devices, media and/or member that may be used to convey, house, support or otherwise facilitate the use of another device, device component, combination of devices, media and/or member. Exemplary non-limiting carriers include drill strings of the coiled tube type, of the jointed pipe type and any combination or portion thereof. Other carrier examples include casing pipes, wirelines, wireline sondes, slickline sondes, drop shots, downhole subs, bottom-hole assemblies, and drill strings.

Figure 2:
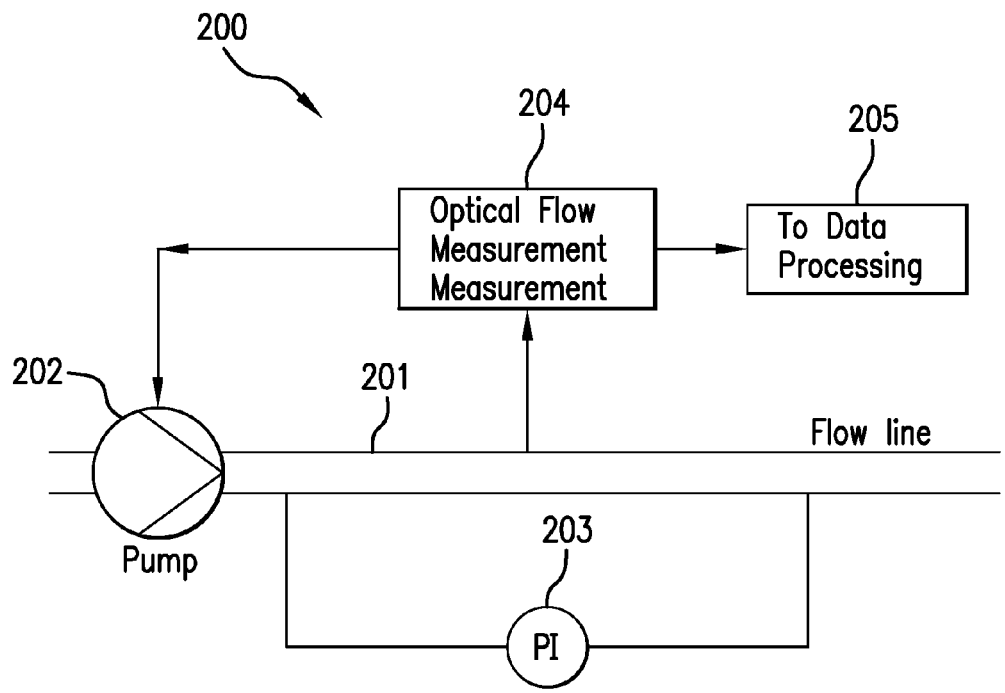
FIG. 2 is a schematic diagram of a first embodiment of a viscometer.

FIG. 2 is a schematic diagram of a first exemplary configuration of a viscometer 200 configured to be disposed with the downhole tool 10. The viscometer 200 includes a tube or flow line 201 through which sampled fluid is advanced. Sampled fluid includes any borehole fluid. As described herein, "borehole fluid" includes any fluid encountered in the borehole 12, which may include one or more of drilling mud or any fluid pumped from the surface as well as any fluid from the formation such as water, natural gas, hydrocarbons or any combination thereof. A pump 202 governs flow rate. In one embodiment, the pump 202 is configured to advance fluid through the flow line 201 in an at least substantially constant rate. An exemplary pump is an electric displacement pump. A pressure gauge 203 such as a differential pressure transducer is used to measure the pressure difference "Δp" across a portion of the tube 201. An optional flow measurement system, such as an optical measurement system 204 may be used to determine flow rate. In one embodiment, the pump 202 is an electric displacement pump, and the position of a piston in the pump may be used to estimate the flow rate. This system can be used to regulate pump rate and/or to provide data for further processing 205. The pump 202 and pressure transducer 203 will normally also have connections to a data processing apparatus 205, such as a surface or downhole processing unit, but such connections are not shown for simplicity of drawing.

Figure 3:
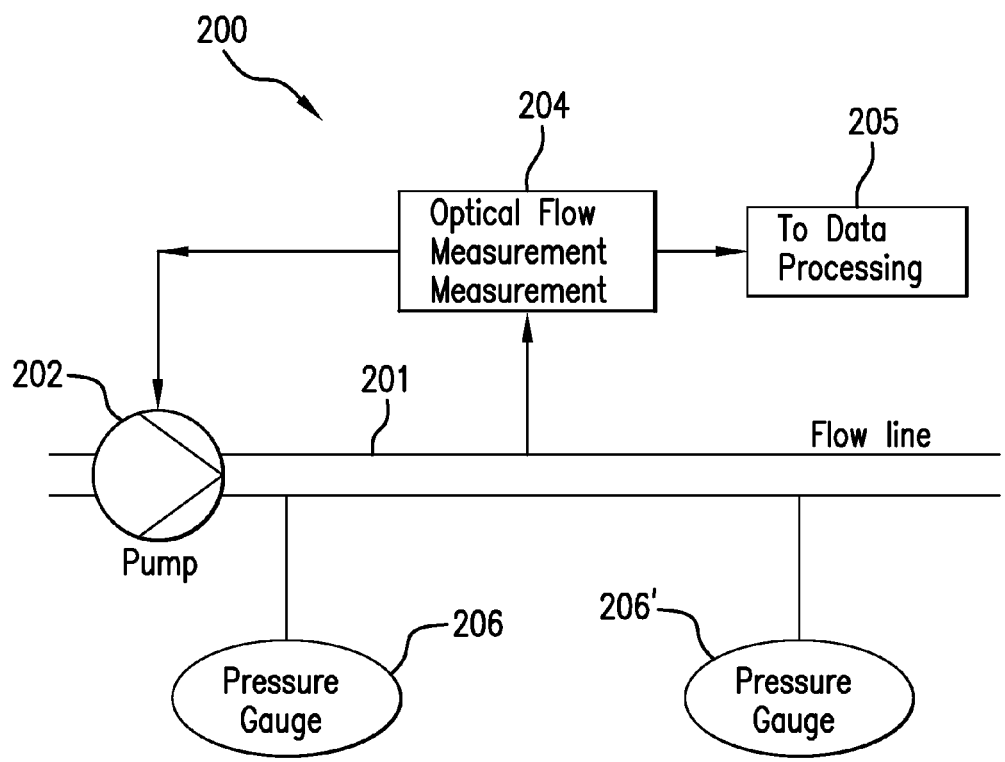
FIG. 3 is a schematic diagram of a second embodiment of embodiment of a viscometer.

FIG. 3 is a schematic diagram of an alternate embodiment of a viscometer configured to be disposed with the downhole tool 10 that includes two pressure gauges 206 and 206', rather than a single, differential pressure gauge 203.

In addition to the embodiments of FIGS. 2 and 3, any type of capillary viscometer may be used. For the purposes of the present application, a capillary viscometer will be defined as any viscometer that determines viscosity of a fluid based on measurement of differential pressure through a tube, or a viscometer that determines pressure and/or fluid flow and/or fluid velocity in a capillary tube.

Figure 4:
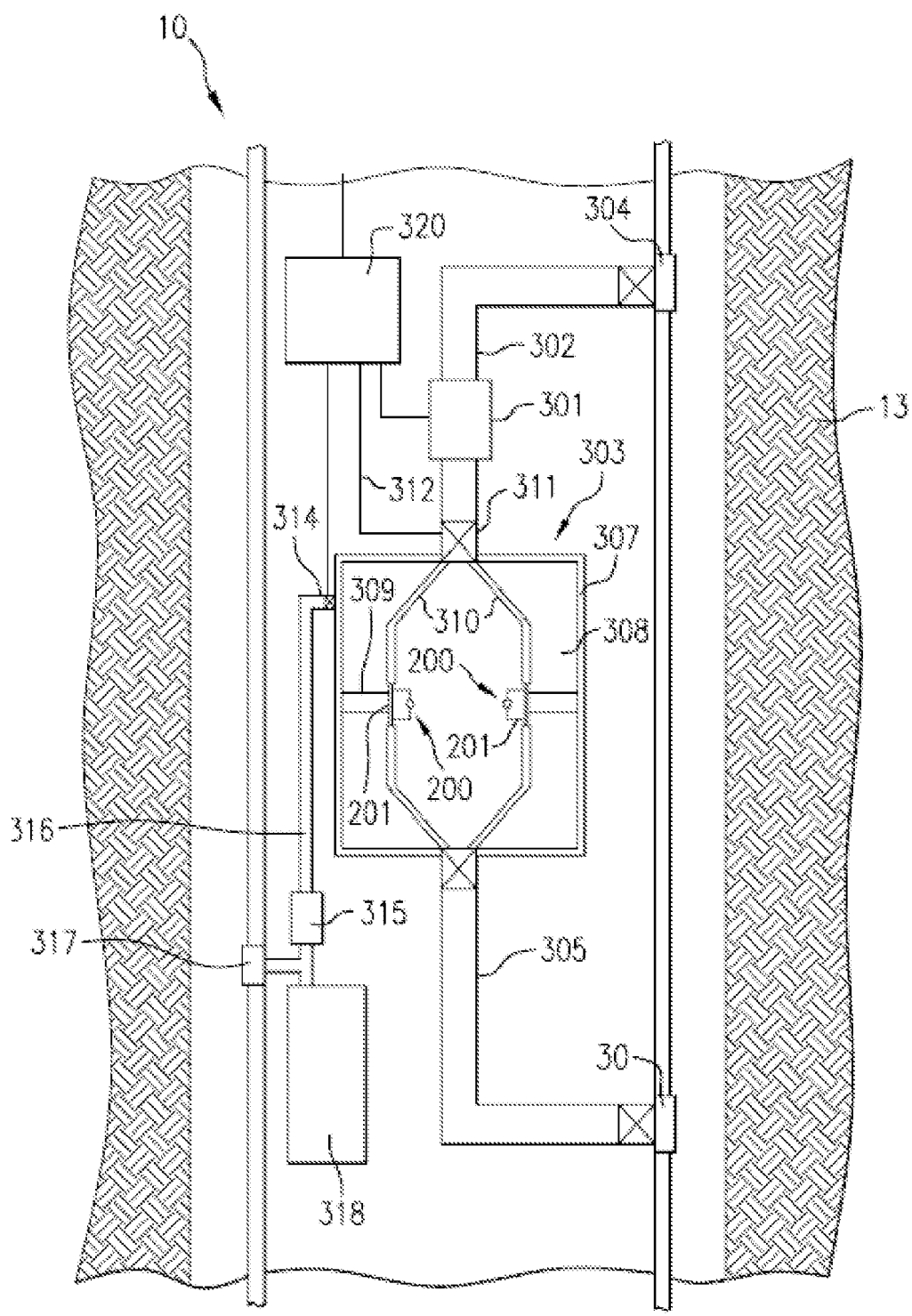
FIG. 4 illustrates an embodiment of a system for measuring downhole fluid viscosity.
Figure 5:
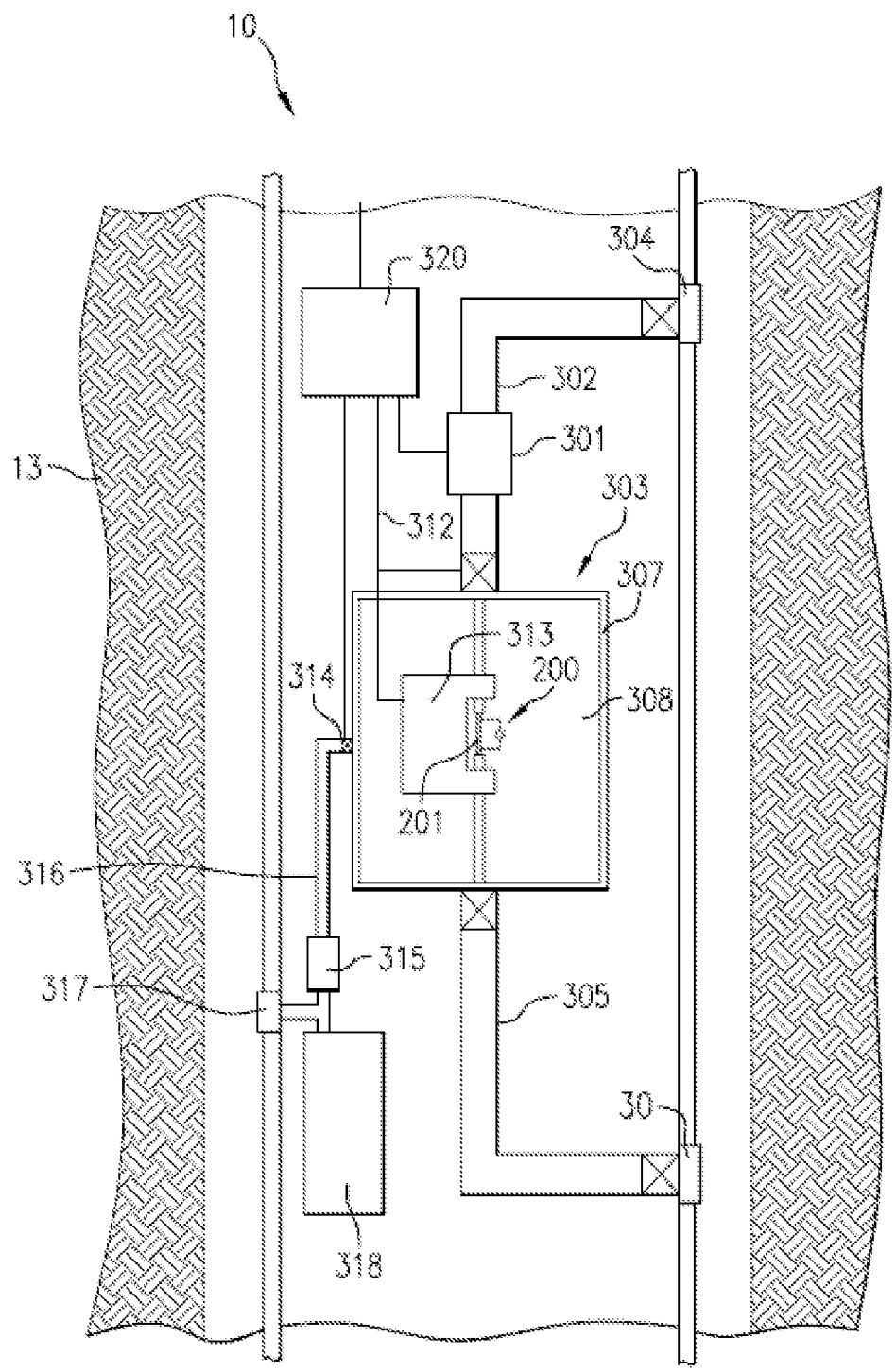
FIG. 5 illustrates another embodiment of a system for measuring downhole fluid viscosity.

FIGS. 4 and 5 are cross-sectional illustrations of embodiments of the downhole tool 10 that include a pump 301 for flushing or otherwise advancing borehole fluids through a passage or conduit 302 and into a measurement unit 303. A fluid input port 304 may be included that couples with borehole fluid and is in fluid connection with the conduit 302. The fluid input port 304 includes any suitable configuration to allow borehole fluid to be drawn into the conduit 302 and the measurement unit 303. An output conduit 305 may be coupled to the measurement unit 303 to allow borehole fluid to flow out of the measurement unit 303. In one embodiment, an output port 306 is in fluid communication with the output conduit 305 to allow borehole fluid to be discharged back into the borehole.

The measurement unit 303 includes one or more viscometers 200 to which borehole fluid is directed from the conduit 302. In one embodiment, the measurement unit includes multiple viscometers 200, pressure gauges 203 and/or tubes 201 to allow the tool 10 to change various properties of the viscometer being used to measure fluid properties.

In one embodiment, the measurement unit 303 includes a housing 307 that defines a cavity 308 in which multiple viscometers 200 are disposed. A supporting apparatus 309 supports at least the viscometer tube 201 and positions the tube 201 in fluid communication with a corresponding fluid passage 310 that fluidly connects each tube 201 to a valve unit 311 that directs fluid from the conduit 302 into individual tubes 201. The supporting apparatus 309 is shown in a simplified fashion for ease of drawing, but will normally contain devices associated with viscosity measurement, such as electronics, a pump, and a pressure gauge. The supporting apparatus 309 may, optionally, be in operable connection with one or more mechanisms for replacing and/or altering the tube 201, such as a heater for cleaning or a coating release device. In addition, the mechanisms may be configured to replace and/or alter multiple viscometers 200 or multiple gauges having different sensors with a different measurement range to cover a desired viscosity range.

Referring to FIG. 4, in one embodiment, a diversion assembly such as the valve assembly 311 is disposed in fluid communication with the conduit 302 and the fluid passages 310 to allow borehole fluid to be individually diverted to each fluid passage 310 and corresponding viscometer tube 201. In addition, the fluid passages 310 may also be connected to multiple viscometers 200 having different sensors with a different measurement range to cover a desired viscosity range. The valve assembly 311 is configured to be actuated to divert borehole fluid individually to one or more fluid passages 310.

A power and/or communication connection, such as an electrical or optical cable 312 is connected to the electronic module 22 and/or data processing apparatus 24, which is configured to control the valve assembly 311 and optionally other components, such as the pump 301. The electronic module 22 and/or data processing apparatus may also be connected to pressure gauges 203, 206 for receiving measurement data. In one embodiment, a downhole processor 320 is connected to the valve assembly 311 and/or the pressure gauges 203, 206 and includes suitable electrical components for facilitating downhole tests, information processing, and/or storage. The downhole processor 320 may include components such as a microprocessor, a memory unit for storing programs and data received from the pressure gauges, and transmitter and receiver circuits.

Referring to FIG. 5, in one embodiment, the measurement unit 303 includes a replacement system configured to exchange or alternate multiple tubes and/or viscometers. The replacement system includes an assembly such as a rotating cylindrical housing 313 that include multiple viscometers 200 or viscometer tubes 201. In one example, the rotating housing includes multiple tubes 201 (having various properties such as length, diameter, interior coatings) arrayed circumferentially around a central axis of the rotating housing 313. The controller 320 or surface controllers are connected to the housing 313 to rotate a tube 201 into fluid communication with a fluid passage 310. Although the configuration shown in FIG. 5 illustrates a pressure gauge or gauges common to each tube 201, in some embodiments, multiple gauges may also be disposed in the rotating housing 313 so that tube properties and/or gauge properties can be changed.

Each viscometer 200 may be given a unique combination of tube dimensions, tube coatings, and pump characteristics. The number and configuration of viscometers 200 is a matter of design choice and is not limited to the configurations described herein. A processing device such the processor 320 or a surface processor may determine which viscometer is giving the best measurements at any given time, based on turbulence and resolution considerations, and may choose measurements from that viscometer.

In one embodiment, the measurement unit 303 is configured to maintain an at least substantially constant pressure within the cavity or otherwise control the pressure to reduce or eliminate pressure variations from the environment surrounding the viscometer(s) 200. The measurement unit 303 may also include other protective features such as a heat sink or cooling device to regulate the temperature of the viscometers or otherwise protect the viscometers from the borehole environment. For example, additional pressure measurement devices are positioned inside the cavity 308 to measure the ambient pressure surrounding the viscometers 200. The controller 320 or other electronics device is connected to a pressure regulating valve 314 that is controlled to allow a fluid to be flowed into the cavity 308 or removed from the cavity by a suitable pump 315. An additional passage or conduit 316 is provided in connection with the valve 314 and the pump 315, and may be connected to a source of fluid, such as a port 317 and/or a fluid reservoir 318. In this way, pressure may be adjusted to maintain a substantially constant pressure in the environment surrounding the viscometers 200 and/or viscometer tubes 201. The configuration described herein is exemplary, as any suitable configuration for regulating pressure surrounding the viscometers 200 or tubes 201 may be used.

Figure 6:
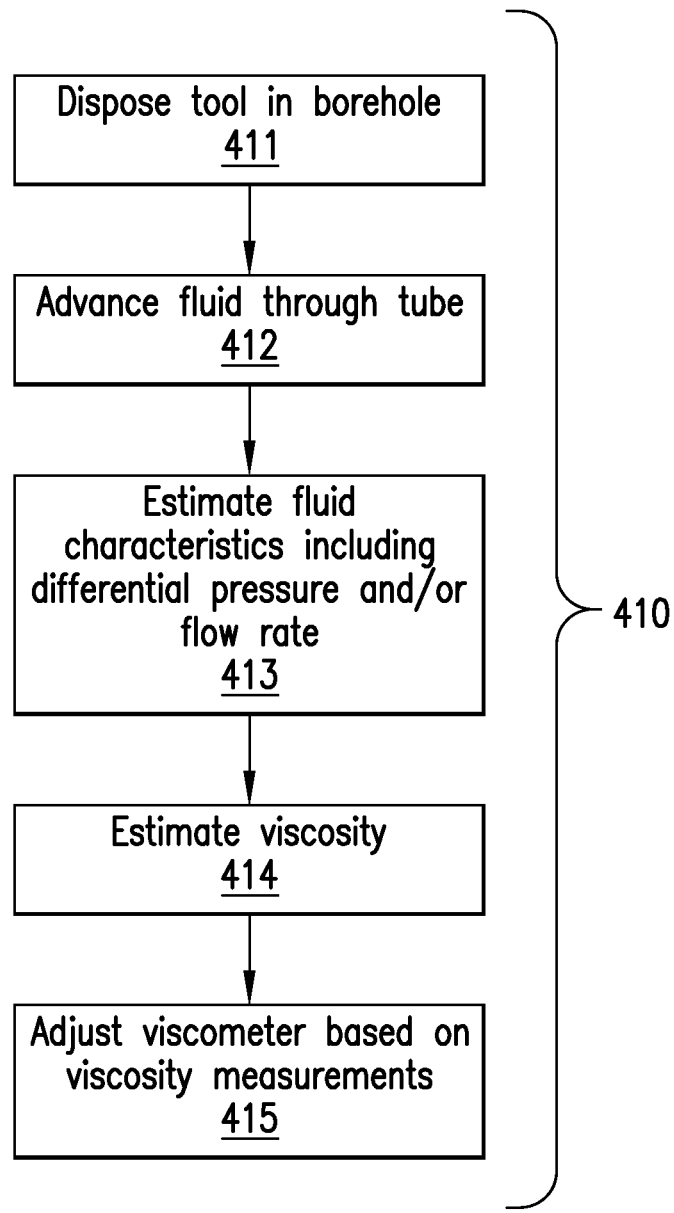
FIG. 6 is a flow chart showing an embodiment of a method of estimating viscosity characteristics of a downhole fluid.

FIG. 6 illustrates a method 410 of estimating viscosity characteristics of a downhole fluid. The method 410 may be performed in conjunction with the downhole tool 10, but is not limited thereto. The method 410 may be used in conjunction with any apparatus or configuration capable of estimating fluid characteristics related to viscosity. The method 410 includes one or more stages 411-415. In one embodiment, the method 410 includes the execution of all of the stages 411-415 in the order described. However, certain stages may be omitted, stages may be added, or the order of the stages changed.

In the first stage 411, the downhole tool 10 is disposed in a borehole, and borehole fluid is advanced through the downhole tool 10, for example, through the conduit 302.

In the second stage 412, downhole fluid is advanced through a capillary or other tube 201 in the downhole tool 10. In one embodiment, a pump 301 such as an electric motor driven displacement pump is used to advance the fluid. For example, the downhole fluid is advanced through the measurement unit 303 and through a viscometer and/or tube 201 that has been selected via the valve assembly 311 or the rotating housing 313.

In the third stage 413, fluid characteristics including flow rate and differential pressure are estimated. The differential pressure is estimated, in one embodiment, via the differential pressure transducer 203 or transducers 206 and 206'. In one embodiment, a displacement pump is utilized and the flow rate is proportional to the motor speed. The flow rate can thus be estimated based on the motor speed.

In one embodiment, in order to improve the accuracy of the pressure transducer or the pressure transducers, the pressures should be in the upper half of the transducer's measurement range. In order to increase the viscosity range under these restrictions, the flow rate can be adapted by a closed loop control system, which controls the speed of the pump motor.

In the fourth stage 414, the viscosity of the borehole fluid is estimated based on the differential pressure. In one embodiment, dynamic viscosity is estimated based on the application of Hagen-Poiseuille's law per equation (1) discussed below. A downhole or surface processor may be utilized to perform stages 412, 413 and/or 414.

Viscosity is the property of a fluid to flow under shear stress. The more viscous a fluid, the higher its resistance to flow. Viscosity is caused by internal friction based on inter-molecular forces, such as Van-der-Waals forces. Fluids may be categorized into two main groups: Newtonian and non-Newtonian fluids. Crude oil belongs predominately to the Newtonian fluids. These fluids have a constant viscosity independent of shear stress and shear rate.

A constant flow through a tube can be described by Hagen-Poiseuille's law, where the fluid is Newtonian and the flow is laminar, per equation (1) below:

$$\dot{V} = \frac{\pi r^4 \Delta p}{8 \eta L} \Rightarrow \eta = \frac{\pi r^4 \Delta p}{8 \dot{V} L} \qquad (1)$$

where $\Delta p$=differential pressure [Pa], r=tube radius [m], L=length of tube [m], $\dot{V}$=volumetric flow [m3/s], and $\eta$=dynamic viscosity [Pa·s].

In this equation, the dynamic viscosity is based on the pressure drop along a tube with a constant volume flow. As shown in the above equation, the radius r of the tube tends to influence results strongly, because it is taken to the power of four. A potential alteration of the radius by fouling effects will therefore have disproportionate impact. Such fouling can be avoided, for example by special coatings on the inner surface of the tube or an extra heating to clean the tube after a certain number of measurements.

In the fifth stage 415, adjustments to the viscometer may be made based on the viscosity measurements. Adjustments include, for example, adjustments to the tube radius, fluid flow rate, tube length and/or pressure gauge resolution. For example, if the viscosity cannot be determined with a sufficient resolution, such adjustments can be made and the viscometry measurement repeated. In one embodiment, such adjustments are performed by changing the viscometer 200 and/or tube 201 through which borehole fluid is advanced to make the viscosity measurement. Such changes can be performed by mechanisms such as those described in conjunction with FIGS. 4 and 5.

Figure 7:
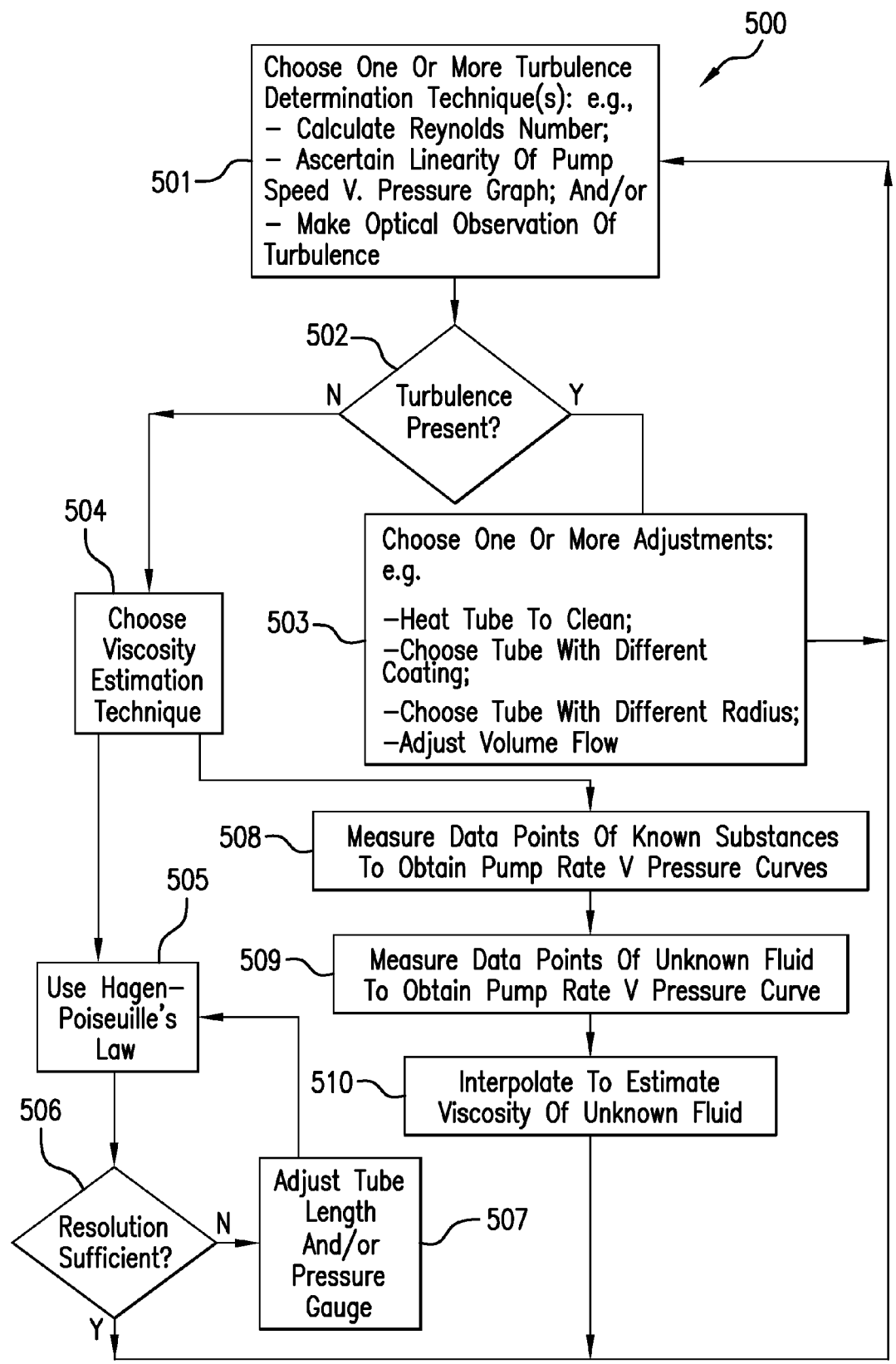
FIG. 7 is a flow chart showing an embodiment of a method of estimating viscosity characteristics of a downhole fluid.

FIG. 7 is a flow chart schematically illustrating an embodiment of a method 500 of estimating fluid viscosity. In one embodiment, the method 500 is performed in conjunction with a viscometer in accordance with the configurations of FIGS. 2, 3, 4 and/or 5.

At stage 501, some determination relating to presence or absence of turbulence is made—absence of turbulence being a condition precedent to determining viscosity in accordance with Hagen-Poiseuille's law. Several approaches may be utilized for ascertaining presence or absence of turbulence. One is calculation of the Reynolds per equation (2) described below. A second approach is optical observation or measurement of the fluid flowing in the tube. A third approach is taking measurements of pressure as a function of pump speed, to determine if the relationship is linear. The skilled artisan may devise other approaches as well. More than one approach might be chosen simultaneously or sequentially. Different approaches might be attempted during different iterations.

In one embodiment, determining whether or not a flow is laminar includes calculation of the Reynolds number per equation (2) below:

$$Re = \frac{\rho \cdot w \cdot d}{\eta} = \frac{w \cdot d}{v} \qquad (2)$$

where Re=Reynolds number [–], w=fluid velocity [m/s], d=characteristic dimension [m], v=kinematic viscosity [m$^2$/s], and $\rho$=density [kg/m$^3$]

Typically, turbulent flow occurs for Reynolds numbers bigger than 2000. The Hagen-Poiseuille equation, equation (1) above, is only valid for laminar flow. One way to make sure that flow is laminar is to verify that the Reynolds number is lower than 2000. With special coatings on the inner surface of the tube, it is possible to increase the Reynolds number without getting turbulent flow. Methods of increasing the Reynolds number include polishing, applying coatings such as diamond-like carbon (DLC), polytetrafluoroethylene, nano-coatings, and any other materials or techniques that reduce or minimize the roughness of the interior surface of the viscometer tube.

If turbulence is found to be present at stage 502, it will be desirable to make adjustments to reduce or at least substantially eliminate turbulence at stage 503. These adjustments could include one or more of cleaning the tube via heating;

coating the tube or choosing a tube with a different coating;

choosing a tube with a different radius; and changing the pumping rate to affect volume flow.

The skilled artisan may devise other adjustments to reduce turbulence. As described above, selection of different tubes may be accomplished via mechanisms such as the valve assembly 311, the rotating housing 313 or other suitable mechanisms.

One method of adjusting or optimising tube dimensions is to iterate between the equations (1) and (2), with each calculation of Reynolds number being informed by an improved calculation of viscosity. Preferably such iteration will increase resolution at very small viscosity values, within constraints imposed by limitations of the pressure gauge. At very high absolute pressures—up to 30,000 psi—a differential pressure of 1 psi or less can be measured. The following considerations may influence selected adjustments to improve the quality of measurement:

Tube radius should be minimized, but with decreasing tube diameters the risk of plugging increases.

Length of the tube has no influence on the Reynolds number, but increases resolution of viscosity numbers.

The better the resolution of the differential pressure gauge, the better the results and the higher the resolution for viscosity values.

Fluid velocity depends on the volume flow and should be reduced as much as possible to achieve low Reynolds numbers; but higher resolution of the viscometer will result from higher volume flow rates. Thus optimal volume flow will result from a tradeoff between these two considerations.

Control will then return to stage 501 to reassess turbulence related determinations.

If turbulence is not found to be present, a technique for estimating viscosity is chosen at stage 504. One technique is the application of Hagen-Poiseuille's law per equation (1) at stage 505. It may be that resolution is not sufficient at stage 506, in which case adjustments can be made at stage 507, such as changing tube length and/or pressure gauge resolution, and calculation repeated.

Another technique for measuring viscosity is interpolation between graphs of pump rate v. pressure for fluids of known viscosity. This technique may be utilized in place of other techniques in which typically no pump at all is used for tube viscometers, instead the natural gravity is forcing the flow. Fluids may behave differently under conditions of extreme temperature and pressure that exist in a borehole. Consequently, it may be desirable to transport samples of known fluids downhole and test those fluids at stage 508 to determine how their pressure curves vary as a function of pump rate at stage 509. Viscosity of unknown fluid sampled from the borehole can then be interpolated from the known fluids at stage 510 based on pump rate v. pressure data taken from the unknown fluid.

Subsequent to stages 506 and 510, viscosity measurements may be output (not shown) and control returns to stage 501. This iteration can be undertaken for more than one reason. The iteration could simply be to take more measurements, possibly at different locations in the borehole. In addition, the iteration would be desirable if the Reynolds number calculation at stage 501 is chosen as a method for ascertaining the presence of turbulence, because the Reynolds number is dependent on viscosity. In this way measurement of viscosity could inform the determination of turbulence in an iterative manner. Though the flowchart is written as an infinite loop, the skilled artisan will understand how to impose exit conditions where desirable.

Figure 8:
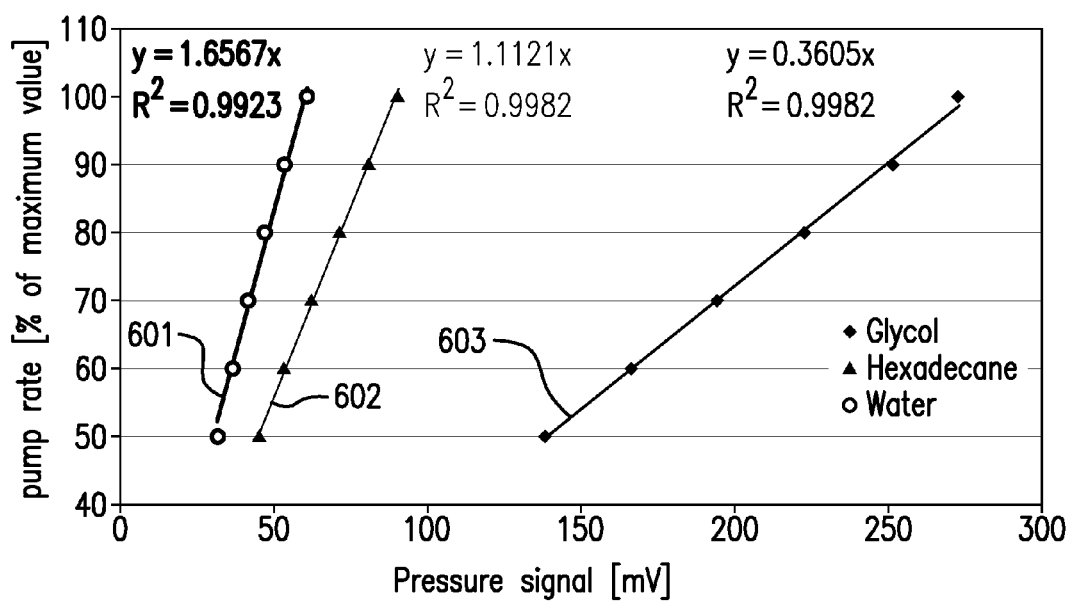
FIG. 8 is a graph of testing results.

Exemplary results of viscosity measurements performed according to the methods described herein are shown in FIG. 8. In this example, the method was performed using a differential pressure gauge and a hose pump. Three different model substances were tested: water, hexadecane and glycol. All experiments were performed at ambient pressure and temperature.

FIG. 8 shows the results for different fluids as a function of the pump rate and the pressure signal. The lowest graph derived viscosity value will be from graph 601, relating to water, with hexadecane 602 and glycol 603 having graph-derived viscosity values that are progressively larger, respectively, than water. The functions of pump rate v. pressure signal are linear for all three substances (indicating laminar flow), with all curves being lines through the origin. This is as would be expected from equation 1. The viscosity is described by the gradient:

$$\dot{V} = m \cdot \Delta p \text{ with } m = \frac{\pi \cdot r^4}{8 \cdot L \cdot \eta} \quad (3)$$

Besides the pressure and the volume flow, the viscosity is only dependent on geometric parameters like radius and length of the tube. The correlation coefficient of the acquired functions is higher than 0.99 for each fluid which indicates the accuracy of this measurement technique.

In one embodiment, viscosities of unknown fluids could be determined using a database of different fluids with known viscosities. As the curves for different fluids are distinctive, the viscosity of any unknown fluid can be estimated using interpolation techniques. To create such a database, additional experiments using fluids with known viscosity characteristics can be performed. In field experiments, the standard TESTRAK or fluid analyser tool pump may be applied.

The apparatuses and methods described herein have various advantages over prior art apparatuses and techniques. The apparatuses and methods allow for accurate estimations of fluid viscosity in high pressure environments such as downhole environments. In addition, the apparatuses and methods described herein reduce the number of moving parts required for viscosity determinations, which can be particularly advantageous for applications such as drilling processes where strong vibrations can be present.

The singular article "a" or "an" as used herein should not be viewed as excluding a plurality of elements. Use of ordinal numbers, such as "first" or "second," is for distinguishing otherwise identical terminology, and is not intended to imply that operations or steps must occur in any particular order, unless otherwise indicated.

Where software or hardware is disclosed, it may be drawn with boxes in a drawing. These boxes may in some cases be conceptual. They are not intended to imply that functions described with respect to them could not be distributed to multiple operating entities; nor are they intended to imply that functions could not be combined into one module or entity—unless otherwise indicated.

In connection with the teachings herein, various analyses and/or analytical components may be used, including digital and/or analog systems. The system may have components such as a processor, storage media, memory, input, output, communications link (wired, wireless, pulsed mud, optical or other), user interfaces, software programs, signal processors (digital or analog) and other such components (such as resistors, capacitors, inductors and others) to provide for operation and analyses of the apparatus and methods disclosed herein in any of several manners well-appreciated in the art. It is considered that these teachings may be, but need not be, implemented in conjunction with a set of computer executable instructions stored on a computer readable medium, including memory (ROMs, RAMs), optical (CD-ROMs), or magnetic (disks, hard drives), or any other type that when executed causes a computer to implement the method of the present invention. These instructions may provide for equipment operation, control, data collection and analysis and other functions deemed relevant by a system designer, owner, user or other such personnel, in addition to the functions described in this disclosure.

One skilled in the art will recognize that the various components or technologies may provide certain necessary or beneficial functionality or features. Accordingly, these functions and features as may be needed in support of the appended claims and variations thereof, are recognized as being inherently included as a part of the teachings herein and a part of the invention disclosed.

While the invention has been described with reference to exemplary embodiments, it will be understood by those skilled in the art that various changes may be made and equivalents may be substituted for elements thereof without departing from the scope of the invention. In addition, many modifications will be appreciated by those skilled in the art to adapt a particular instrument, situation or material to the teachings of the invention without departing from the essential scope thereof. Therefore, it is intended that the invention not be limited to the particular embodiment disclosed as the best mode contemplated for carrying out this invention.

The invention claimed is:

1. A method for measuring viscosity in a borehole comprising:
pumping downhole fluid through at least one tube disposed in a carrier configured to be disposed in a borehole in an earth formation;
taking at least one differential pressure measurement of the fluid in the at least one tube via a pressure transducer; and
estimating a viscosity of the fluid based on the at least one differential pressure measurement and a fluid flow rate, wherein estimating the viscosity includes deriving at least one data set representing a relationship between differential pressure and fluid flow rate, obtaining one or more known data sets representing relationships between differential pressure and fluid flow rate, the known data sets corresponding to fluids having known viscosity characteristics, and deriving the viscosity by comparing the at least one data set to one or more of the known data sets.

2. The method of claim 1, wherein estimating includes ascertaining a presence or absence of turbulence in the at least one flow line.

3. The method of claim 2, wherein the fluid flow rate is derived from at least one known parameter selected from at least one of a tube radius, a tube length and pressure transducer resolution.

4. The method of claim 2, wherein taking at least one differential pressure measurement includes altering one or more of the at least one known parameter to optimise measurement.

5. The method of claim 3, wherein taking the at least one differential pressure measurement includes:
ascertaining whether turbulence is present in the fluid in the at least one tube;
altering one or more of the at least one known parameter responsive to a positive result of the ascertaining, the positive result indicating that turbulence is present; and
iterating the ascertaining and the altering until turbulence is at least substantially absent.

6. The method of claim 1, wherein estimating the viscosity includes:
ascertaining whether turbulence is present in the fluid in the at least one tube; and
iterating between ascertaining and estimating the viscosity, to refine an estimate of the viscosity, wherein iterating includes, in response to ascertaining that turbulence is present, adjusting a parameter of at least one of the pumping and the pressure transducer, estimating the viscosity based on the adjusted parameter, and repeating the ascertaining.

7. The method of claim 1, wherein estimating the viscosity includes calculating the viscosity of the fluid using Hagen-Poiseuille's law.

8. The method of claim 2, wherein estimating the viscosity includes:
deriving at least one data curve representing a relationship between differential pressure and fluid flow rate,
obtaining known data curves corresponding to fluids having known viscosity characteristics; and
deriving the viscosity by comparing the at least data curve to one or more of the known data curves.

9. An apparatus for measuring viscosity of a fluid in a borehole comprising
a carrier configured to be disposed in a borehole in an earth formation, the carrier including at least one tube configured to contain at least one sample of the fluid;
at least one pump configured to establish flow in the at least one tube;
at least one pressure transducer configured to measure a differential pressure in each of the at least one tube; and
a processor configured to estimate a viscosity of the fluid based on the differential pressure measurement and a fluid flow rate, wherein estimating the viscosity includes deriving at least one data set representing a relationship between differential pressure and fluid flow rate, obtaining one or more known data sets representing relationships between differential pressure and fluid flow rate, the known data sets corresponding to fluids having known viscosity characteristics, and deriving the viscosity by comparing the at least one data set to one or more of the known data sets.

10. The apparatus of claim 9, wherein estimating includes ascertaining a presence or absence of turbulence in the at least one flow line.

11. The apparatus of claim 10, wherein the processor is configured to estimate the fluid flow rate based on a pumping rate for each of the at least one pump, wherein the fluid flow rate is proportional to a speed of the at least one pump.

12. The apparatus of claim 9, wherein the at least one pressure transducer includes at least one pair of first and second pressure transducers adapted to measure the at least one respective differential pressure.

13. The apparatus of claim 9, wherein the processor is configured to estimate viscosity based on Hagen-Poiseuille's law.

14. The apparatus of claim 10, wherein the processor is configured to estimate the viscosity based on comparing:
at least one data curve representing a relationship between differential pressure and fluid flow rate, and
known data curves corresponding to fluids having known viscosity characteristics.

15. The apparatus of claim 9, further comprising a mechanism configured to select one of a plurality of tubes responsive to the presence of turbulence.

16. The apparatus of claim 9, wherein the processor is configured to change a rate of pumping in the at least one pump responsive to the presence of turbulence.

17. The apparatus of claim 11, wherein the at least one pump is a displacement pump, and the processor is configured to estimate the fluid flow rate based on a motor speed of the displacement pump.

18. The apparatus of claim 11, further comprising a mechanism configured to replace at least one of the pressure transducer and the at least one tube with at least one of a second pressure transducer and a second tube in fluid communication with the at least one pump.

19. The apparatus of claim 18, wherein the mechanism is selected from a valve assembly and a rotating housing configured to hold a plurality of pressure transducers and/or tubes.

20. An apparatus for measuring viscosity of a fluid in a borehole comprising:
- a carrier configured to be disposed in a borehole in an earth formation, the carrier including at least one tube configured to contain at least one sample of the fluid;
- at least one pump configured to establish flow in the at least one tube;
- at least one pressure transducer configured to measure a differential pressure in each of the at least one tube; and
- a processor configured to estimate a viscosity of the fluid based on the differential pressure measurement; and a fluid flow rate derived from at least one known parameter, wherein estimating the viscosity includes deriving at least one data curve representing a relationship between differential pressure and fluid flow rate, obtaining known data curves corresponding to fluids having known viscosity characteristics, and deriving the viscosity by comparing the at least data curve to one or more of the known data curves.

* * * * *